United States Patent [19]

Fleischle

[11] Patent Number: Plant 5,814

[45] Date of Patent: Dec. 2, 1986

[54] DISTINCT VARIETY OF STREPTOCARPUS NAMED NANCY

[75] Inventor: Gerhard Fleischle, Vaihingen/E.-Ensingen, Fed. Rep. of Germany

[73] Assignee: Oglevee Associates, Inc., Connellsville, Pa.

[21] Appl. No.: 699,456

[22] Filed: Feb. 7, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new variety of Streptocarpus plant is characterized by its large flowers and large open throat area. It is further characterized by its multi-coloring and penciling. It has long permanence and is generally nonfertile.

1 Drawing Figure

BACKGROUND OF THE NEW PLANT

The present invention comprises a new and distinct cultivar of Streptocarpus X hybridus known by the varietal name of Nancy. The new cultivar is a mutation brought about by the irradiation of an unpatented Streptocarpus known by the varietal name Carmen. The new cultivar is similar to Carmen in respect of plant form and growth characteristics and is different from Carmen in respect of color.

The new cultivar is generally characterized by its large flowers, multi-coloring and penciling and its large open throat. It has long permanence and is generally nonfertile.

The new cultivar was discovered July 2, 1981 in Vaihingen, Federal Republic of Germany; was first asexually reproduced by cuttings in Vaihingen, Federal Republic of Germany; and has been repeatedly asexually reproduced by cuttings at Oglevee Floral Company in Connellsville, Pa. It has been found to retain its distinctive characteristics through successive propagations.

The new cultivar, when grown in a greenhouse in Connellsville, Pa., has a response time of nine weeks from a well-rooted young plant in a 2¼ inch pot to a flowering plant in a 6 inch pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth the characteristics of the new cultivar. The data which define these characteristics were collected from asexual reproductions carried out by the Oglevee Floral Company in Connellsville, Pa. The plant history was taken on nine week plants blossomed under natural light in a greenhouse and color readings were taken indoors under 100 foot candles of cool white fluorescent light. Color references are to the R.H.S. colour chart of The Royal Horticultural Society of London unless noted differently.

Botanical classification: Gesneriaceae (Family): *Streptocarpus* X *hybridus* (Genus X species).

Flower:

*Fully expanded.*—8 centimeters.

*Borne.*—In clusters of one to three flowers per flower stalk above the foliage. Flower stalk arises from mid-rib of each leaf.

*Stem.*—Single, long, pubescent and slightly flattened.

*Form.*—Funnel formed in an umbel.

*Permanence.*—Long lasting 21 to 25 days.

Color:

*Tonality from a distance.*—Rose 38 with purple 39 penciling and mimosa 2 throat (Exotica III).

*Front of petals.*—Predominant color is Fan 2 Red Purple Group 73B which fades into Fan 2 Red Purple Group 72D at outer petal edges and base of petals. Penciling is Fan 2 Red Purple Group 74B from throat to mid-petal area.

*Reverse of petals.*—Fan 2 Red Purple Group 70D.

*Throat.*—Fan 1 Yellow Group 8B.

*Discoloration.*—Darkens with age.

Petals:

*Texture.*—Flat textured generally but changing to a slightly velvet texture in throat.

*Appearance.*—Individually lobed with cuneate ruffled margins.

*Arrangement.*—Regularly united into an elliptical form.

*Persistence.*—21 to 25 days and remains on plant in dry form until picked.

*Fragrance.*—None.

Reproductive organs:

*Anthers.*—Two per flower, attached and imperfect; slightly purple cast.

*Filament.*—Attached to petals for a distance of 2 centimeters up from base and then free standing for 1 centimeter.

*Pollen.*—Generally nonfertile.

*Pistil.*—2.5 centimeters long.

*Style.*—White, 1 centimeter long.

*Stigma.*—White, flattened with reflexed tips.

*Ovaries.*—1.5 centimeters long; brownish purple cast.

Plant:

*Form.*—Leaves rosette from a crown at the soil line.

*Growth.*—A spreading, free flowing habit with leaves being elliptical.

*Height from soil line.*—15 centimeters.
*Spread.*—30 to 45 centimeters.

Foliage:

*Size.*—10 to 28 centimeters in length; 5 to 10 centimeters wide at widest point.
*Quantity.*—10 to 15 leaves.
*Shape.*—Elliptical.
*Top side.*—Fan 3 Green Group 137B.
*Under side.*—Fan 3 Green Group 139D.
*Ribs and veins.*—Pinnate.

*Ribs and vein color.*—Fan 3 Yellow Green Group 145C.
*Margin.*—Cuneate and some ruffling.
*Leaf tips.*—Obtuse.
*Leaf base.*—Acute.

I claim:

1. A new and distinct variety of Streptocarpus substantially as herein shown and described.

* * * * *

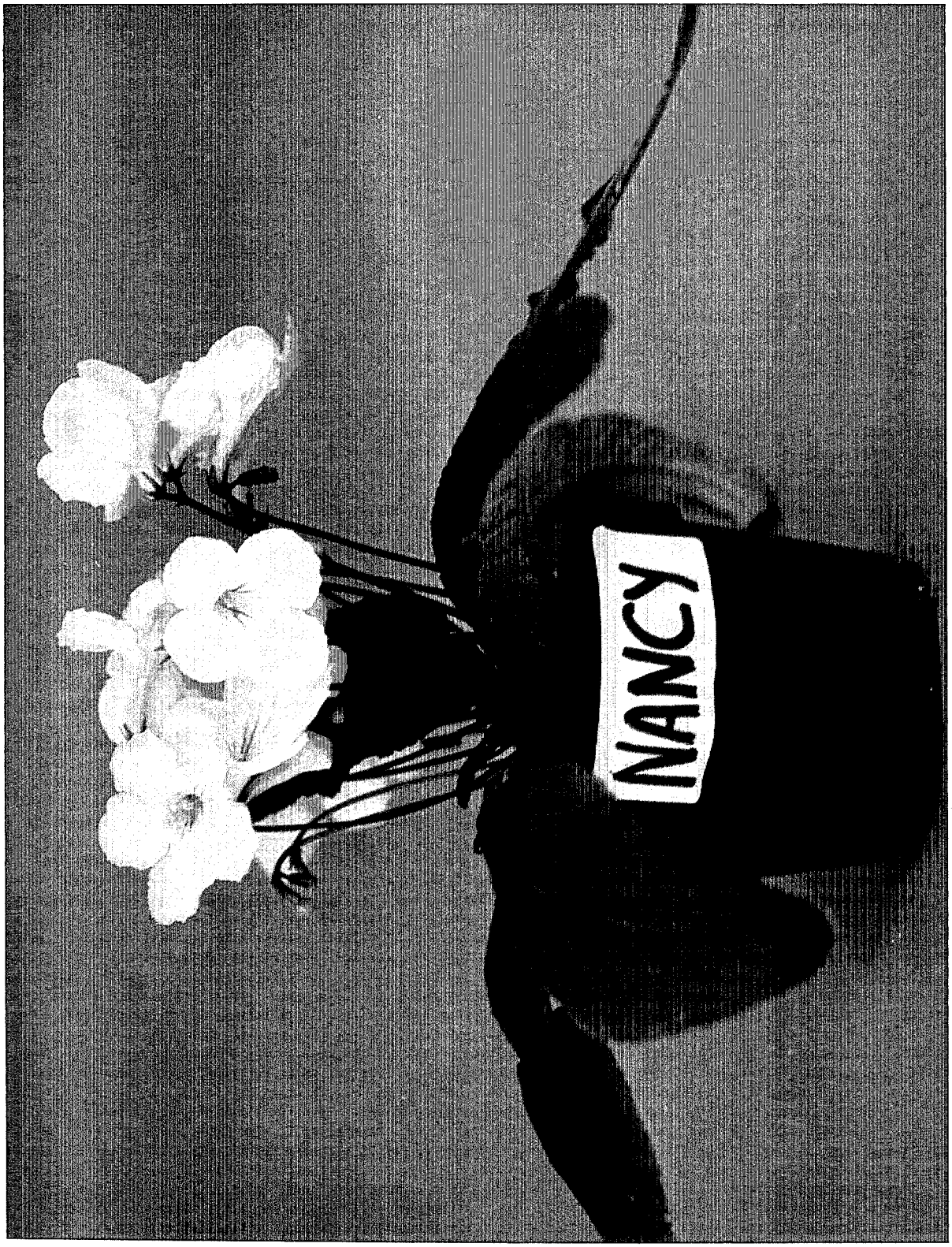
NANCY